(12) United States Patent
Thoren et al.

(10) Patent No.: US 9,770,272 B2
(45) Date of Patent: Sep. 26, 2017

(54) ORTHOPEDIC COMPRESSION/DISTRACTION DEVICE

(71) Applicant: Wright Medical Technology, Inc., Memphis, TN (US)

(72) Inventors: Brian Thoren, Memphis, TN (US); Daniel McCormick, Bartlett, TN (US); Wesley Reed, Libertyville, IL (US); Thomas Cramer, Gainesville, FL (US); Gary Lowery, Eads, TN (US); David Harness, Eads, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 476 days.

(21) Appl. No.: 14/212,882

(22) Filed: Mar. 14, 2014

(65) Prior Publication Data

US 2014/0228899 A1 Aug. 14, 2014

Related U.S. Application Data

(63) Continuation-in-part of application No. 13/712,300, filed on Dec. 12, 2012, now Pat. No. 9,078,710.
(Continued)

(51) Int. Cl.
*A61B 17/58* (2006.01)
*A61B 17/60* (2006.01)
(Continued)

(52) U.S. Cl.
CPC .............................. *A61B 17/7077* (2013.01)

(58) Field of Classification Search
CPC ..... A61B 17/025; A61B 17/885; A61B 17/70; A61B 17/7014; A61B 17/7077; Y10T 403/32008; Y10T 403/32254
(Continued)

(56) References Cited

U.S. PATENT DOCUMENTS

| 554,284 A | 2/1896 | Lorang |
| 575,631 A | 1/1897 | Brooks |

(Continued)

FOREIGN PATENT DOCUMENTS

| CH | 303453 | 5/1952 |
| CH | 02709/94-3 | 9/1994 |

(Continued)

OTHER PUBLICATIONS

International Search Report and Written Opinion issued on Aug. 14, 2014 for corresponding PCT Application No. PCT/US2014/028641.
(Continued)

*Primary Examiner* — Kevin T Truong
*Assistant Examiner* — Si Ming Ku
(74) *Attorney, Agent, or Firm* — Duane Morris LLP

(57) ABSTRACT

An orthopedic device configured for use as a compressor or a distractor is provided. The device has two arm members and a locking sleeve for securely holding an elongated pin is attached to each of the two arm members. The locking sleeve are hingeably connected to the outer end of each of the two arm members by a biaxial hinge block, wherein the biaxial hinge block is configured to allow the locking sleeve to swivel in two different directions about two orthogonally oriented axes.

18 Claims, 13 Drawing Sheets

Related U.S. Application Data

(60) Provisional application No. 61/782,759, filed on Mar. 14, 2013.

(51) Int. Cl.
*A61F 2/00* (2006.01)
*A61B 17/70* (2006.01)

(58) Field of Classification Search
USPC .................. 606/105, 60, 246–279; 600/201, 600/231–234
See application file for complete search history.

(56) References Cited

U.S. PATENT DOCUMENTS

| | | |
|---|---|---|
| 1,271,792 A | 7/1918 | Standish |
| 1,563,242 A | 11/1925 | Tweit |
| 1,920,821 A | 8/1933 | Wassenaar |
| 2,250,417 A | 7/1941 | Ettinger |
| 2,251,209 A | 7/1941 | Stader |
| 2,346,346 A | 4/1944 | Anderson |
| 2,391,537 A | 12/1945 | Anderson |
| 2,391,693 A | 12/1945 | Ettinger |
| 2,393,694 A | 1/1946 | Kirschner |
| 2,393,831 A | 1/1946 | Stader |
| 2,427,128 A | 9/1947 | Ettinger |
| 2,774,271 A | 12/1956 | Mano |
| 2,876,027 A | 3/1959 | Sulmonetti |
| 2,932,029 A | 4/1960 | De Nicolo |
| 3,044,512 A | 7/1962 | Jones |
| 3,154,331 A | 10/1964 | Engelhardt |
| 3,195,380 A | 7/1965 | Bicks |
| 3,509,882 A | 5/1970 | Blake |
| 3,828,791 A | 8/1974 | Santos |
| 3,961,854 A | 6/1976 | Jaquet |
| 4,135,505 A | 1/1979 | Day |
| 4,170,990 A | 10/1979 | Baumgart et al. |
| 4,187,840 A | 2/1980 | Watanabe |
| 4,220,146 A | 9/1980 | Cloutier |
| 4,227,826 A | 10/1980 | Conrad |
| 4,349,018 A | 9/1982 | Chambers |
| 4,364,381 A | 12/1982 | Sher et al. |
| 4,457,307 A | 7/1984 | Stillwell |
| 4,475,546 A | 10/1984 | Patton |
| 4,483,334 A | 11/1984 | Murray |
| 4,487,203 A | 12/1984 | Androphy |
| RE31,809 E | 1/1985 | Danieletto et al. |
| 4,501,266 A | 2/1985 | McDaniel |
| 4,524,766 A | 6/1985 | Peterson |
| 4,548,199 A | 10/1985 | Agee |
| 4,567,886 A | 2/1986 | Peterson |
| 4,570,625 A | 2/1986 | Harris et al. |
| 4,611,586 A | 9/1986 | Agee et al. |
| 4,620,533 A | 11/1986 | Mears |
| 4,624,250 A | 11/1986 | Saunders et al. |
| 4,635,634 A | 1/1987 | Santos |
| 4,666,109 A | 5/1987 | Fallon et al. |
| 4,696,293 A | 9/1987 | Ciullo |
| 4,700,437 A | 10/1987 | Hoshino |
| 4,703,751 A | 11/1987 | Pohl |
| 4,712,542 A | 12/1987 | Daniel et al. |
| 4,730,608 A | 3/1988 | Schlein |
| 4,738,253 A | 4/1988 | Buechel et al. |
| 4,785,694 A | 11/1988 | Burmester |
| 4,787,383 A | 11/1988 | Kenna |
| 4,825,857 A | 5/1989 | Kenna |
| 4,848,368 A | 7/1989 | Kronner |
| 4,901,711 A | 2/1990 | Goble et al. |
| 4,922,856 A | 5/1990 | Sweeney, Jr. |
| 4,938,762 A | 7/1990 | Wehrli |
| 4,957,495 A | 9/1990 | Kluger |
| 4,968,316 A | 11/1990 | Hergenroeder |
| 4,998,935 A | 3/1991 | Pennig |
| 5,002,547 A | 3/1991 | Poggie |
| 5,007,912 A | 4/1991 | Albrektsson et al. |
| 5,021,056 A | 6/1991 | Hofman |
| 5,062,844 A | 11/1991 | Jamison et al. |
| 5,152,280 A | 10/1992 | Danieli |
| 5,160,335 A | 11/1992 | Wagenknecht |
| 5,161,534 A * | 11/1992 | Berthiaume .......... A61M 25/01 226/127 |
| 5,167,725 A | 12/1992 | Clark et al. |
| 5,207,676 A | 5/1993 | Canadell et al. |
| 5,219,349 A | 6/1993 | Krag et al. |
| 5,304,177 A | 4/1994 | Pennig |
| 5,312,402 A | 5/1994 | Schlapfer et al. |
| 5,376,090 A | 12/1994 | Pennig |
| 5,403,313 A | 4/1995 | Lin |
| 5,405,347 A | 4/1995 | Lee et al. |
| RE34,985 E | 6/1995 | Pennig |
| 5,429,637 A | 7/1995 | Hardy |
| 5,437,666 A | 8/1995 | Tepic et al. |
| 5,443,465 A | 8/1995 | Pennig |
| 5,451,225 A | 9/1995 | Ross, Jr. et al. |
| 5,451,226 A | 9/1995 | Pfeil et al. |
| 5,478,340 A | 12/1995 | Kluger |
| 5,507,760 A | 4/1996 | Wynne et al. |
| 5,545,162 A | 8/1996 | Huebner |
| 5,549,608 A | 8/1996 | Errico et al. |
| 5,586,983 A | 12/1996 | Sanders et al. |
| 5,586,984 A | 12/1996 | Errico et al. |
| 5,624,447 A | 4/1997 | Myers |
| 5,658,283 A | 8/1997 | Huebner |
| 5,662,648 A | 9/1997 | Faccioli et al. |
| 5,662,649 A | 9/1997 | Huebner |
| 5,662,650 A | 9/1997 | Bailey et al. |
| 5,683,389 A | 11/1997 | Orsak |
| 5,690,633 A | 11/1997 | Taylor et al. |
| 5,702,389 A | 12/1997 | Taylor et al. |
| 5,707,370 A | 1/1998 | Berki et al. |
| 5,709,685 A | 1/1998 | Dombrowski et al. |
| 5,728,095 A | 3/1998 | Taylor et al. |
| 5,728,096 A | 3/1998 | Faccioli et al. |
| 5,741,252 A | 4/1998 | Mazzio et al. |
| 5,743,898 A | 4/1998 | Bailey et al. |
| 5,746,741 A | 5/1998 | Kraus et al. |
| 5,752,954 A | 5/1998 | Mata et al. |
| 5,788,695 A | 8/1998 | Richardson |
| 5,810,817 A | 9/1998 | Roussouly et al. |
| 5,823,486 A | 10/1998 | Smith et al. |
| 5,827,282 A | 10/1998 | Pennig |
| 5,891,143 A | 4/1999 | Taylor et al. |
| 5,891,144 A | 4/1999 | Mata et al. |
| 5,931,837 A | 8/1999 | Marsh et al. |
| 5,968,043 A | 10/1999 | Ross et al. |
| 5,971,984 A | 10/1999 | Taylor et al. |
| 5,976,134 A | 11/1999 | Huebner |
| 6,010,501 A | 1/2000 | Raskin et al. |
| 6,024,745 A | 2/2000 | Faccioli et al. |
| 6,030,386 A | 2/2000 | Taylor et al. |
| 6,036,691 A | 3/2000 | Richardson |
| 6,066,142 A | 5/2000 | Serbousek et al. |
| 6,080,153 A | 6/2000 | Mata et al. |
| 6,129,727 A | 10/2000 | Austin et al. |
| 6,168,595 B1 | 1/2001 | Durham et al. |
| 6,171,308 B1 | 1/2001 | Bailey et al. |
| 6,203,575 B1 | 3/2001 | Farey |
| 6,217,577 B1 | 4/2001 | Hofmann |
| 6,221,072 B1 | 4/2001 | Termaten |
| 6,238,400 B1 | 5/2001 | Bays |
| 6,245,071 B1 | 6/2001 | Pierson |
| 6,342,054 B1 | 1/2002 | Mata |
| 6,386,786 B1 | 5/2002 | Perlman et al. |
| 6,461,358 B1 | 10/2002 | Faccioli et al. |
| 6,491,694 B1 | 12/2002 | Orsak |
| 6,503,340 B1 | 1/2003 | Gold et al. |
| 6,613,049 B2 | 9/2003 | Winquist et al. |
| 6,616,664 B2 | 9/2003 | Walulik et al. |
| 6,709,433 B1 | 3/2004 | Schoenefeld |
| 6,793,655 B2 | 9/2004 | Orsak |
| 7,004,943 B2 | 2/2006 | Ferrante et al. |
| 7,011,658 B2 | 3/2006 | Young |
| 8,568,417 B2 | 10/2013 | Petrzelka et al. |
| 2002/0026190 A1 | 2/2002 | Walulik et al. |

(56) References Cited

U.S. PATENT DOCUMENTS

| | | |
|---|---|---|
| 2003/0149429 A1 | 8/2003 | Ferrante et al. |
| 2006/0004380 A1 | 1/2006 | DiDomenico et al. |
| 2006/0235389 A1 | 10/2006 | Albert |
| 2006/0235422 A1 | 10/2006 | Keller |
| 2006/0247645 A1 | 11/2006 | Wilcox et al. |
| 2006/0247649 A1* | 11/2006 | Rezach ............. A61B 17/7077 606/90 |
| 2009/0204115 A1 | 8/2009 | Dees, Jr. |
| 2011/0077690 A1 | 3/2011 | Shin |
| 2011/0245876 A1 | 10/2011 | Brumfield |
| 2012/0029566 A1 | 2/2012 | Rezach |
| 2013/0190731 A1 | 7/2013 | Cude |
| 2014/0012269 A1 | 1/2014 | Bass |
| 2015/0164569 A1 | 6/2015 | Reitblat et al. |

FOREIGN PATENT DOCUMENTS

| | | |
|---|---|---|
| DE | 375151 | 5/1923 |
| DE | 1935977 | 1/1971 |
| DE | 1603999 | 5/1971 |
| DE | 2745504 | 4/1979 |
| DE | 3805178 | 8/1989 |
| DE | 3823746 | 1/1990 |
| DE | 9103480.9 | 6/1991 |
| DE | 4238582 | 5/1994 |
| DE | 29512917 | 11/1995 |
| EP | 0524441 | 6/1992 |
| EP | 0611007 | 8/1994 |
| EP | 0 639 352 A1 | 2/1995 |
| EP | 0700664 | 3/1996 |
| EP | 1021992 | 7/2000 |
| FR | 2665353 | 2/1992 |
| JP | 2015-128581 A | 7/2015 |
| KR | 10-0391252 | 7/2003 |
| NO | 25934 | 6/1915 |
| SU | 167008 | 11/1965 |
| SU | 1491-492 | 8/1986 |
| SU | 1572590 | 6/1990 |
| WO | 88/01152 | 2/1988 |
| WO | 88/03395 | 5/1988 |
| WO | 94/18898 | 9/1994 |
| WO | 96/12443 | 5/1996 |
| WO | 97/10775 | 3/1997 |
| WO | 97/16128 | 5/1997 |
| WO | 98/36698 | 8/1998 |
| WO | 99/29247 | 4/1999 |
| WO | 99/22661 | 5/1999 |
| WO | 00/40163 | 7/2000 |
| WO | 02/053038 A3 | 7/2002 |
| WO | 03/065911 | 8/2003 |

OTHER PUBLICATIONS

Search Report issued on Sep. 2, 2015 in corresponding EP Patent Application No. 15169035.1.

Search Report issued on Dec. 9, 2014 in corresponding PCT Application No. PCT/US2014/028765.

Partial Supplementary European Search Report issued for corresponding European patent application No. 14836955.6, Apr. 13, 2017, 7 pages.

Japanese Office Action issued in corresponding Japanese patent application No. 2016-533291, Mar. 14, 2017, 3 pages.

* cited by examiner

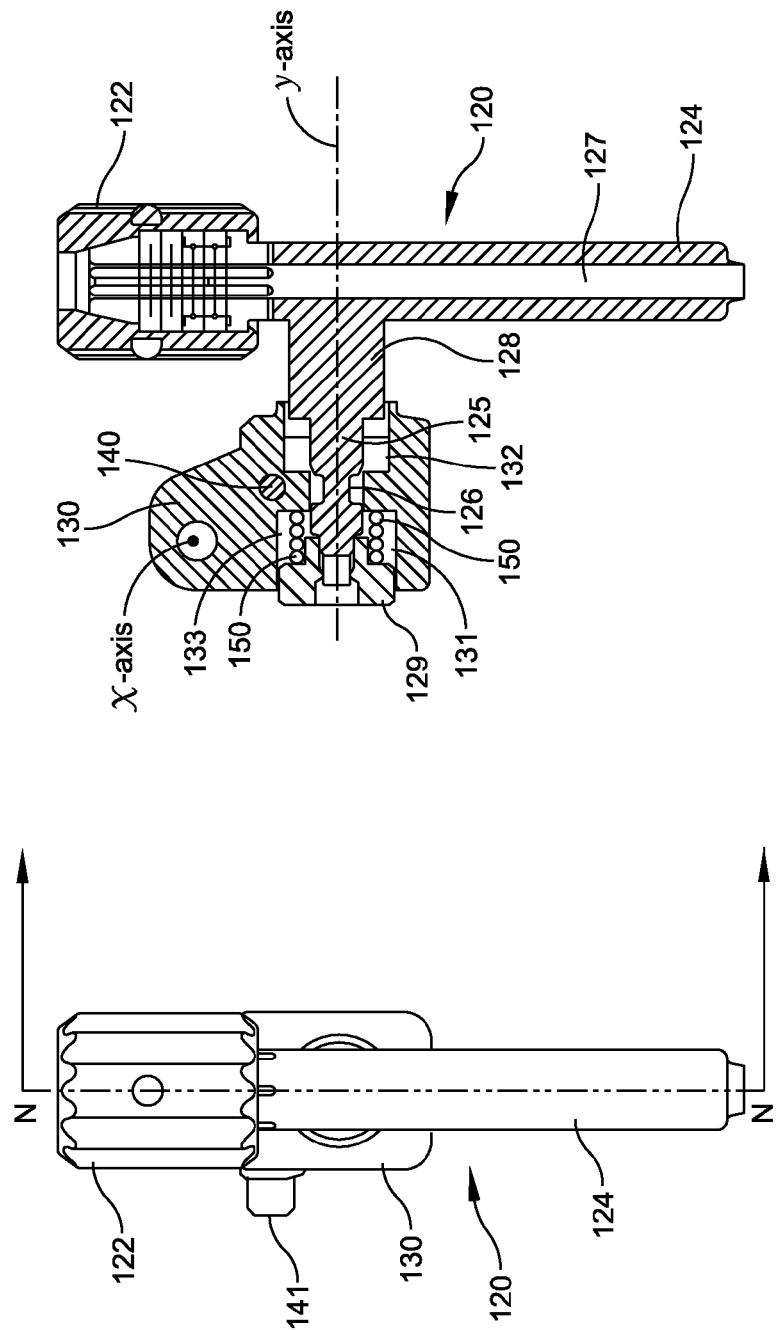

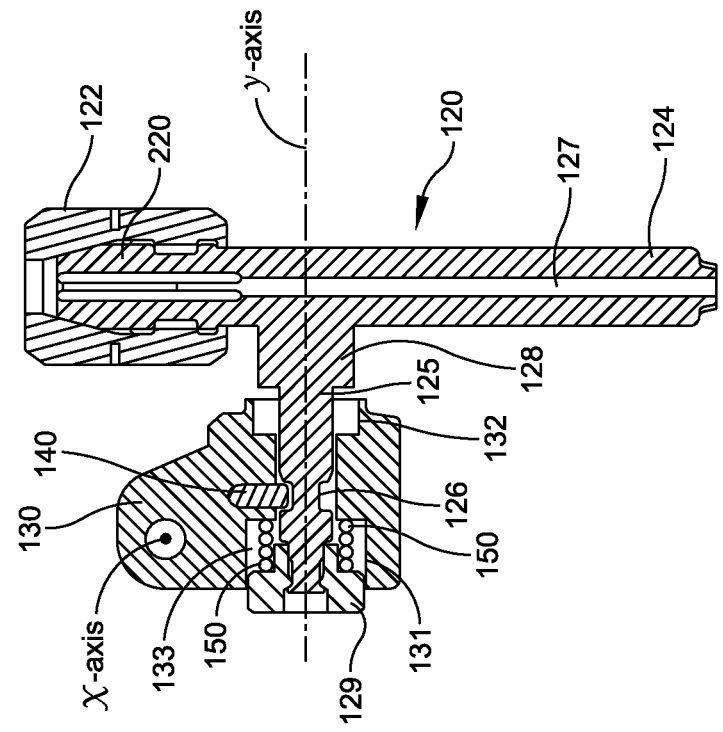
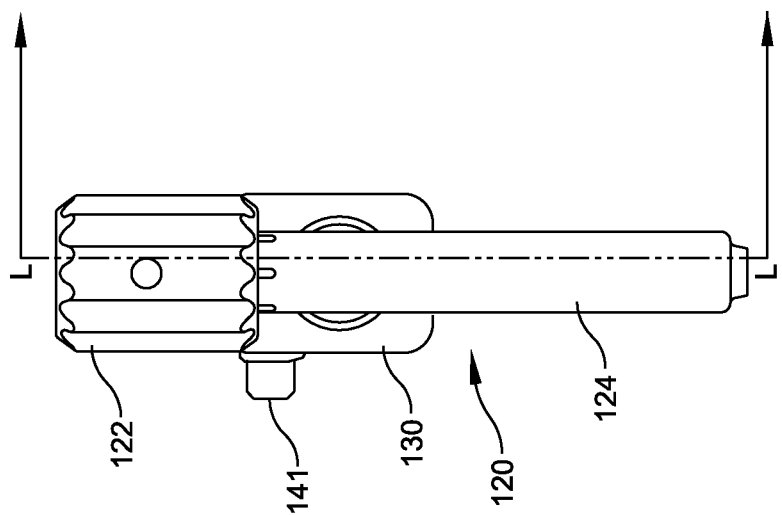
FIG. 7B (unlocked second position)
FIG. 7A (unlocked second position)

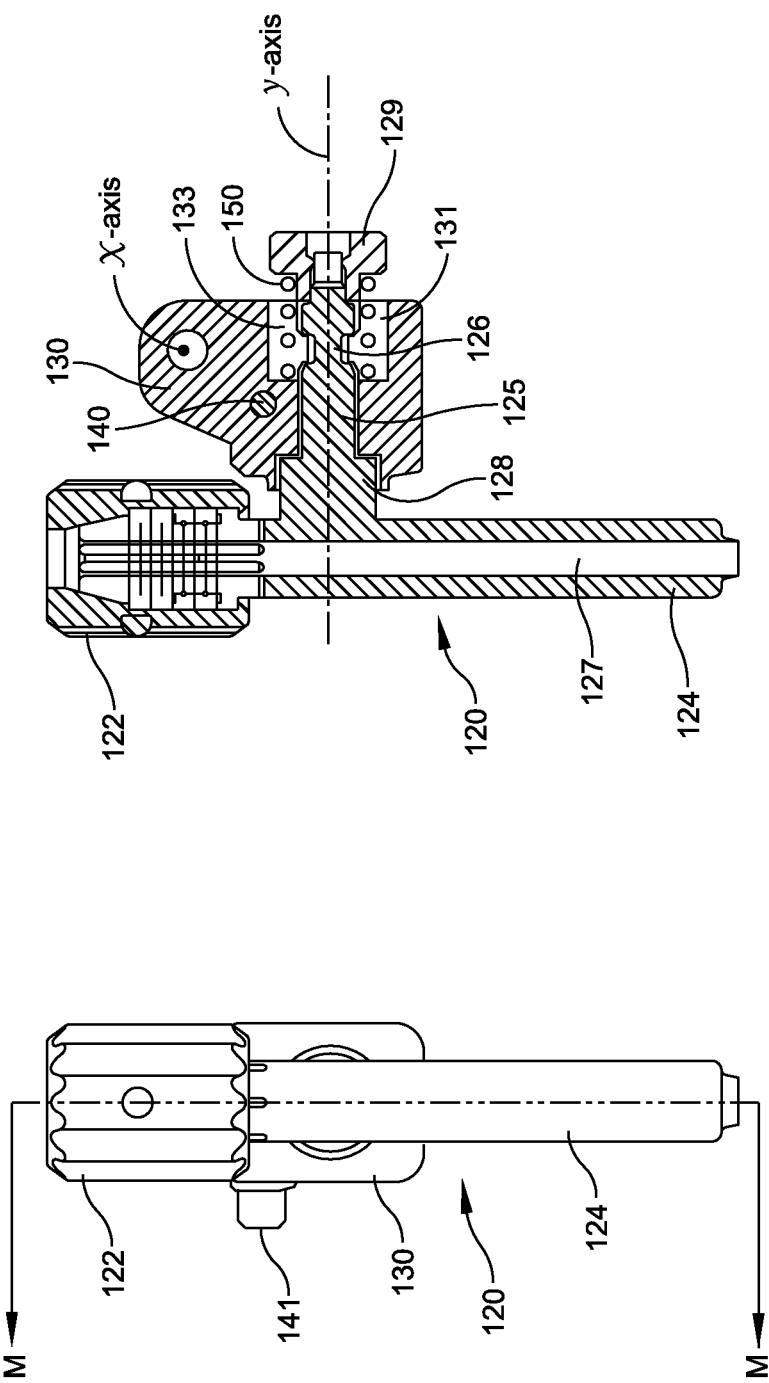

(locked first position)

(locked first position)

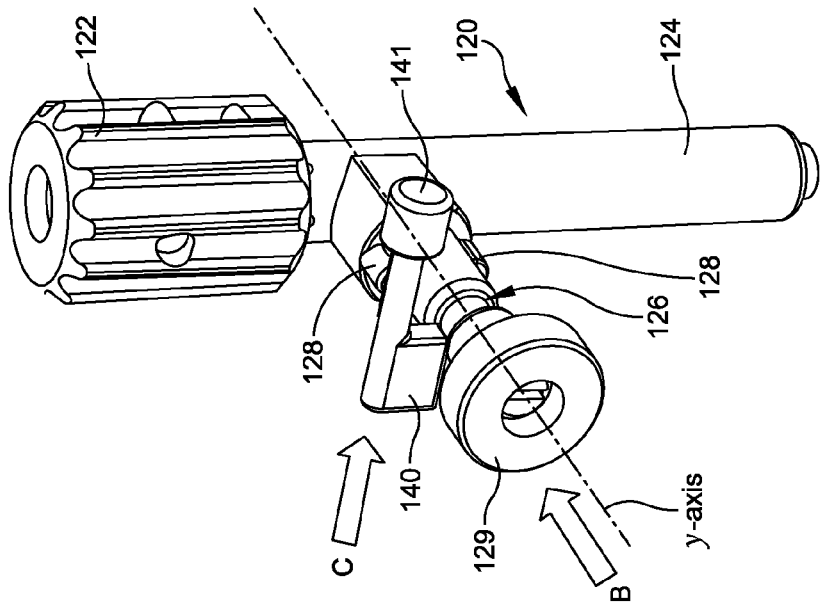
FIG. 10B (unlocked second position)
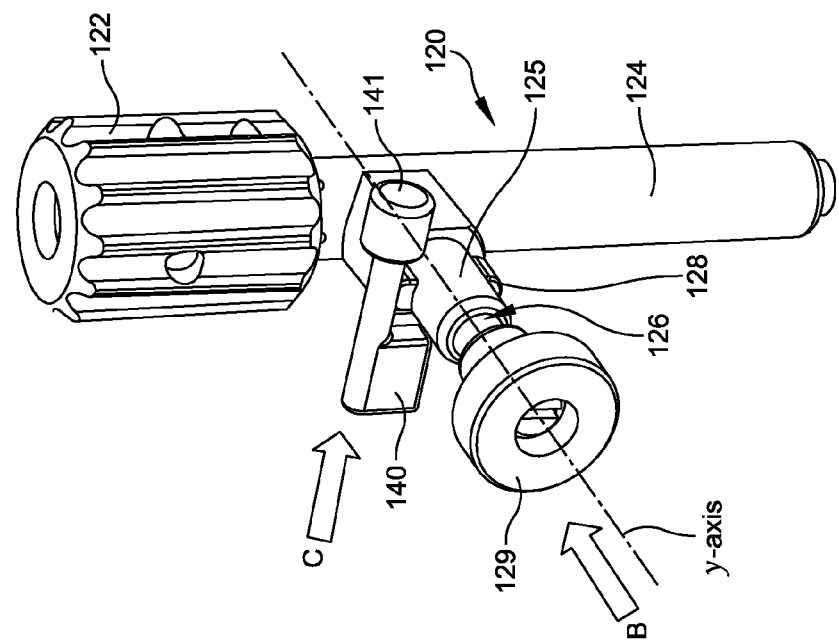
FIG. 10A (locked first position)

(unlocked second position)

(locked first position)

ORTHOPEDIC COMPRESSION/DISTRACTION DEVICE

CROSS-REFERENCE TO RELATED APPLICATION

This application is a continuation-in-part of U.S. patent application Ser. No. 13/712,300, filed on Dec. 12, 2012, the entire contents of which are incorporated herein by reference. This application also claims the benefit under 35 U.S.C. §119(e) of a U.S. Provisional application No. 61/782,759, filed on Mar. 14, 2013.

FIELD OF THE INVENTION

The present disclosure relates to an orthopedic device for compression or distraction of bone parts.

BACKGROUND

Orthopedic devices utilizing elongated pins as fasteners for compression or distraction of bone parts finds many uses for treating orthopedic patients. "Elongated pins" will be used herein to refer to various pins and wires, such as K-wires, used for fixating bone parts or providing anchors. Therefore, there is a continuing need for an improved orthopedic device that expands the scope and ability of the orthopedic surgeons in treating patients in a variety of conditions.

SUMMARY

According to an aspect of the present disclosure an orthopedic device that can be used for compression or distraction of bone parts is described. The orthopedic device comprises an elongated body having first and second ends, a first arm member attached to and transversely extending away from said first end and terminating at an outer end and a second arm member transversely extending away from said elongated body and having a base portion and an outer end. The base portion is configured and adapted to movably engage the elongated body allowing the second arm member to be longitudinally movable along said elongated body. Said second arm member extends from the elongated body in the same direction as the first arm member. The orthopedic device also includes a locking sleeve hingeably connected to the outer end of each of the first and second arm members by a biaxial hinge block, wherein the locking sleeve is configured for receiving and locking on to an elongated pin and the biaxial hinge block is configured to allow each of the locking sleeve to swivel in two different directions with respect to its corresponding arm member about two orthogonally oriented axes.

According to another aspect, an assembly comprising a biaxial hinge block; and a locking sleeve is disclosed. In the assembly, the biaxial hinge block and the locking sleeve are configured to hingeably connect the locking sleeve to an arm member of an orthopedic device, said biaxial hinge block being configured to allow the locking sleeve to swivel in two different directions with respect to the arm member about two orthogonally oriented swivel axes.

BRIEF DESCRIPTION OF THE DRAWINGS

FIG. 6A is an illustration of the locking sleeve connected to the biaxial hinge block viewed along the y-axis showing the plane K-K extending through the center of the locking sleeve along which the cross-sectional view of FIG. 6B is taken.

FIG. 6B is a cross-sectional view along K-K taken through the biaxially swiveling locking sleeve attachment in its swiveling position.

FIG. 7A is the illustration of FIG. 6A showing the plane L-L extending off-center through the locking sleeve along which the cross-sectional view of FIG. 7B is taken.

FIG. 7B is a cross-sectional view along L-L taken through the biaxially swiveling locking sleeve attachment in its swiveling position.

FIG. 8A is the illustration of FIG. 6A showing the plane M-M extending through the center of the locking sleeve along which the cross-sectional view of FIG. 8B is taken.

FIG. 8B is a cross-sectional view along M-M taken through the biaxially swiveling locking sleeve attachment in its non-swiveling position.

FIG. 10A is an illustration of the biaxially swiveling locking sleeve in its non-swiveling position shown with only the y-axis locking pin portion of the biaxial hinge block shown.

FIG. 10B is an illustration of the biaxially swiveling locking sleeve in its swiveling position shown with only the y-axis locking pin portion of the biaxial hinge block shown.

The features shown in the above referenced drawings are illustrated schematically and are not intended to be drawn to scale nor are they intended to be shown in precise positional relationship. Like reference numbers indicate like elements.

DETAILED DESCRIPTION

Figure 1:
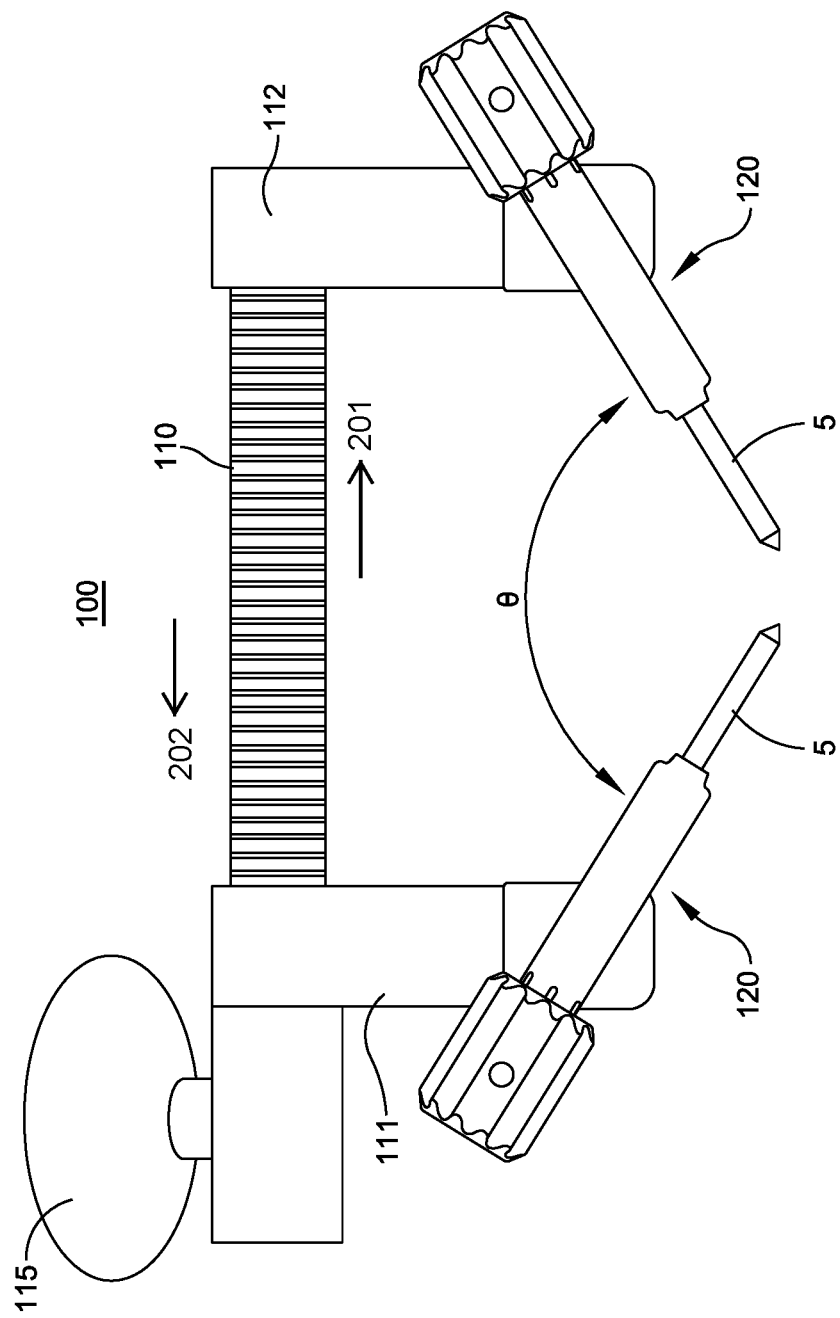
FIG. 1 is an illustration of an orthopedic device according to the present disclosure showing the locking sleeve attachments swiveled toward each other while the orthopedic device is in a distraction mode.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Figure 2A:
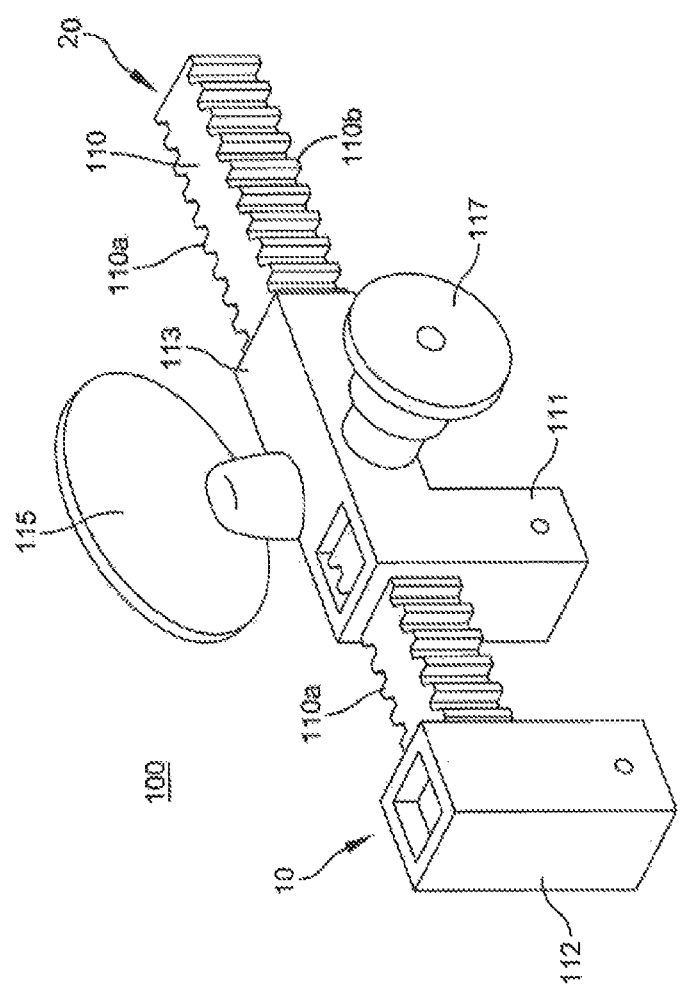
FIG. 2A is an illustration of the orthopedic device of FIG. 1 with the locking sleeve attachments removed.
Figure 2B:
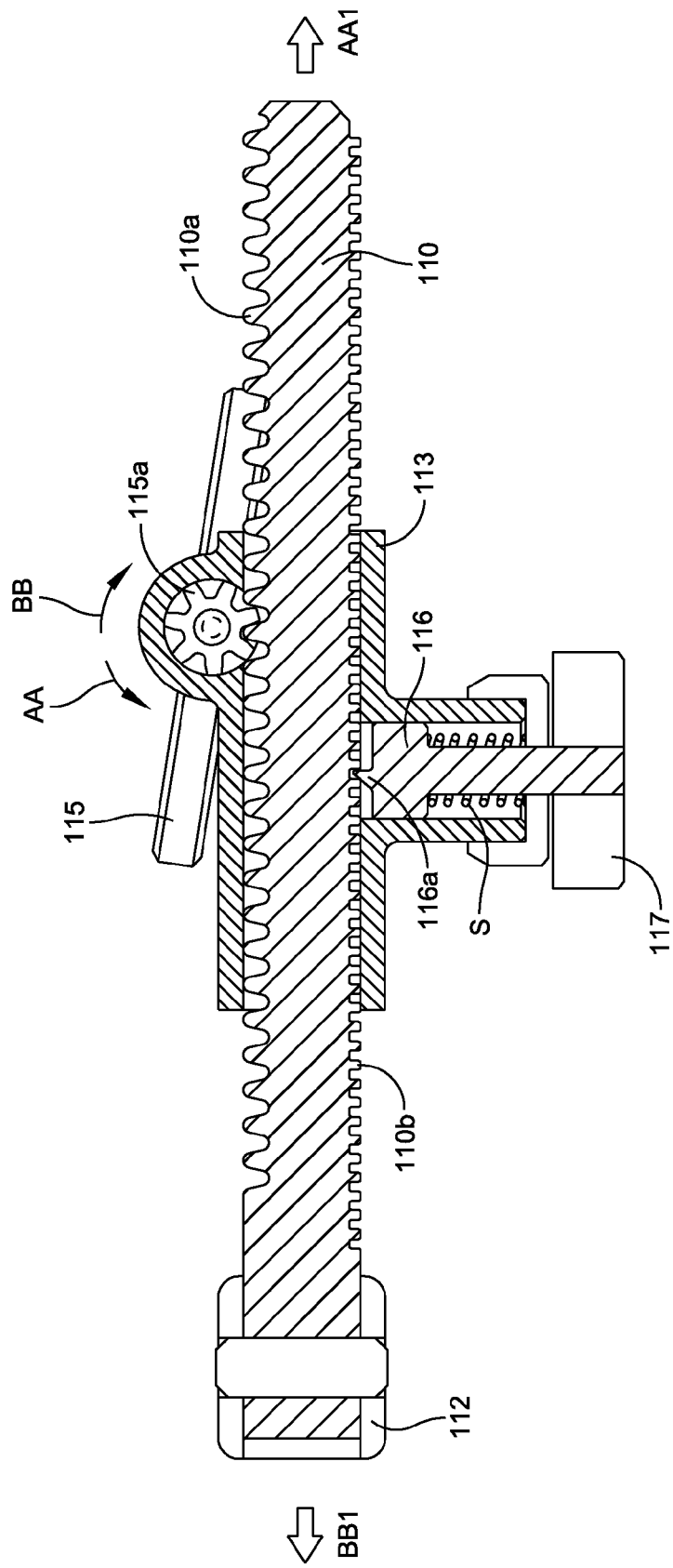
FIG. 2B is an illustration showing the rack-and-pinion mechanism of the orthopedic device of FIG. 1.

FIGS. 1-2B show an orthopedic device 100 that can be used for compression or distraction of bone parts according to an aspect of the present disclosure. The orthopedic device 100 comprises an elongated body 110 having first end 10 and a second end 20. A first arm member 112 extends away from the first end 10 in a direction transverse to the elongated body 110. The first arm member 112 can be integrally formed with the body 110 or otherwise attached to the elongated body 110. A second arm member 111 transversely extends away from the elongated body 110. The second arm member 111 is configured with a base portion 113 that is configured and adapted to movably engage the elongated body 110 allowing the second arm member 111 to be longitudinally movable along the elongated body to accomplish compression or distraction function of the device.

The actual structural mechanism for enabling the movable engagement between the elongated body 110 and the second arm member 111 can be one of many such structures known in the art. Referring to FIG. 2B, in one embodiment, the elongated body 110 is a rack of gear teeth 110a and a pinion gear 115a provided on the base portion 113 engages the rack of gear teeth 110a for longitudinally moving the second arm member 111 along the elongated body. The pinion gear 115a is rotatably attached to the base portion 113 and the second arm member 111 is moved longitudinally by turning the pinion gear 115a. The pinion gear 115a is provided with a bow 115, similar to a bow on a key, to enable a user to turn the pinion gear.

The base portion 113 is configured with ratcheting mechanisms that can selectably operate in compression or distraction mode. For example, the base portion 113 can be provided with a spring-loaded ratcheting pin mechanism 116 for limiting the moving direction of the second arm member 111 along the elongated body 110 to be a one-way movement, as shown in FIG. 2B.

In the configuration shown in FIG. 2B, the spring-loaded ratcheting pin mechanism 116 is arranged so that the ratcheting pin mechanism 116 engages the ratchet teeth 110b by a detent 116a. The coil spring S urges the detent 116a against the ratchet teeth 110b. The detent 116a has a slanted surface on one side as shown so that the ratchet teeth 110b can depress the detent 116a against the spring S and, thus, gliding over the detent 116a. The elongated body 110 can move in the direction of arrow AA1 by turning the pinion gear 115a in the direction of the arrow AA. The detent 116a will prevent the elongated body 110 from moving in the opposite direction shown by the arrow BB1.

In order to move the elongated body 110 in the direction of the arrow BB1, the spring-loaded ratcheting pin mechanism 116 is turned 180 degrees so that the slanted side of the detent 116a is now facing in the opposite direction. This feature is used to change the direction of the one-way movement second arm member 111 so that the operation of the orthopedic device 100 is changed from compression to distraction and vice versa. The spring loaded ratcheting pin mechanism 116 can be turned 180 degrees by pulling the pin mechanism out using the thumb wheel 117, turning it 180 degrees and releasing it. The spring bias will return the pin mechanism 116 to the seated position but with the detent 116a now facing 180 degrees from before. Then, the pinion gear 115a can be turned in the direction of the arrow BB and move the elongated body 110 in the direction of the arrow BB1. Another example of the ratcheting mechanism between the base portion 113 and the elongated body 110 is described in U.S. patent application Ser. No. 13/712,300, filed by the Applicant on Dec. 12, 2012, the contents of which is incorporated herein by reference.

In the orthopedic device 100 according to the present disclosure shown I FIG. 1, locking sleeve 120 attachments are hingeably connected to the outer ends of the first and second arm members 111, 112 by a biaxial hinge block 130 shown in FIGS. 4A-9B. The locking sleeves 120 are configured for receiving and locking on to an elongated pin and the biaxial hinge block 130 is configured to allow each of the locking sleeve to swivel in two different directions with respect to its corresponding arm member, 111 or 112, about two orthogonally oriented axes. The biaxial hinge block 130 is shown and described in detail below in conjunction with FIGS. 4A through 9B.

In FIG. 1, the orthopedic device 100 is in distraction mode and the locking sleeve attachments 120 holding elongated pins 5 are shown swiveled toward each other forming an angle ⊖ between the two locking sleeve attachments 120.

Referring to FIGS. 4A through 5C, the orthopedic device 100 also includes a locking sleeve 120 hingeably connected to the outer end of each of the first and second arm members 111, 112 by a biaxial hinge block 130, wherein each locking sleeve 120 is configured for lockably receiving an elongated pin (not shown).

Figure 12:
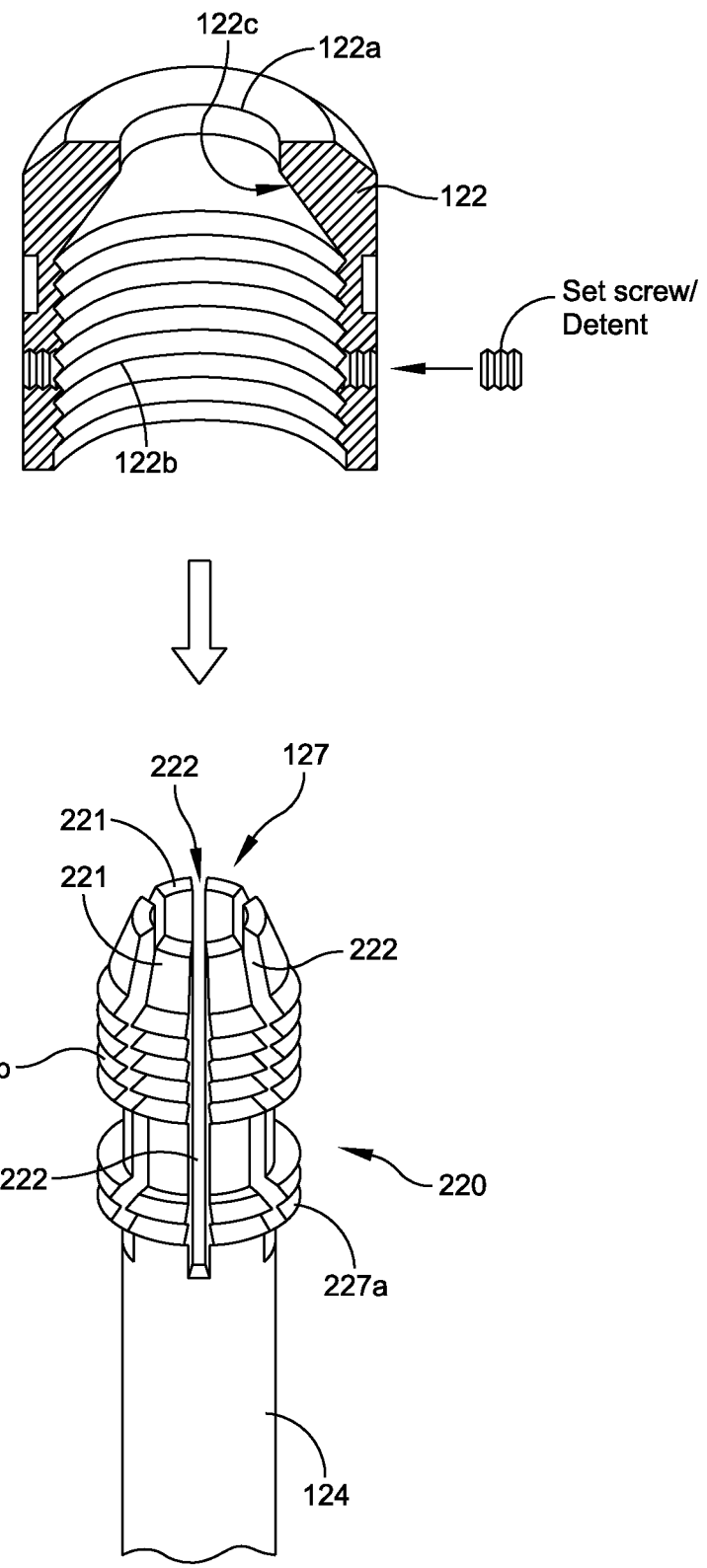
FIG. 12 is an exploded orthographic view showing the threaded collet end of a locking sleeve and a collet nut where the collet nut is shown in cross-section.

The locking sleeve 120 comprises an elongated shaft 124 having an elongated pin receiving bore 127 (see FIGS. 6B, 7B, 8B, 9B) extending therethrough and a threaded collet 220 (see FIG. 7) provided at one end of the elongated shaft for locking onto or securely holding the elongated pin received in the pin receiving bore 127. Referring to FIG. 12, the threaded collet 220 comprises a plurality of collet arms 221, defined by slots 222, provided with screw threads 227a, 227b integrally formed on their exterior surfaces, and a collet nut 122 that is threadably engaged to the threaded collet 220 for locking or securely holding the elongated pin 5 that is received in the elongated pin receiving bore 127.

FIG. 12 shows detailed structures of the threaded collet 220 and the collet nut 122. As shown in the longitudinal cross-section view of the collet nut 122 in FIG. 12, the collet nut 122 is open at one end for receiving the threaded collet 220 and has an interior surface provided with screw threads 122b for threadably engaging the screw threads 227a, 227b of the collet 220. At the end opposite from the threaded collet receiving end, a through hole 122a is provided for the elongated pin received in the elongated pin receiving bore 127. The interior surface of the collet nut 122 is configured with a conical surface 122c for engaging collet arms 221. When an elongated pin 5 is received in the elongated pin receiving bore 127, the threading action of the collet nut 122 causes the collet arms 221 to move radially inward and clamp onto the elongated pin and lock the elongated pin in place. Generally, it is envisioned that the user can lock an elongated pin received in the elongated receiving bore 127 by tightening the collet nut 122 by hand. Further details of the structures of the threaded collet 220 and the collet nut 122 can be found in the U.S. patent application Ser. No. 13/712,300, filed by the Applicant on Dec. 12, 2012, the contents of which are incorporated herein by reference.

As shown in FIGS. 4A through 5B, each of the biaxial hinge blocks 130 is configured to allow the locking sleeve 120 to swivel in two directions about two orthogonally oriented swivel axes, x-axis and y-axis. The biaxial hinge blocks 130 can connect the locking sleeves 120 directly to the outer ends of one of the arm members 111, 112 similar to the way the hinge joints in the orthopedic device disclosed in U.S. patent application Ser. No. 13/712,300 connect the locking sleeves to the outer ends of the arm members 111, 112. In the embodiment of the present disclosure, the outer ends of the arm members 111, 112 are configured for modular connection of the locking sleeves 120 or some other attachments.

Figure 3:
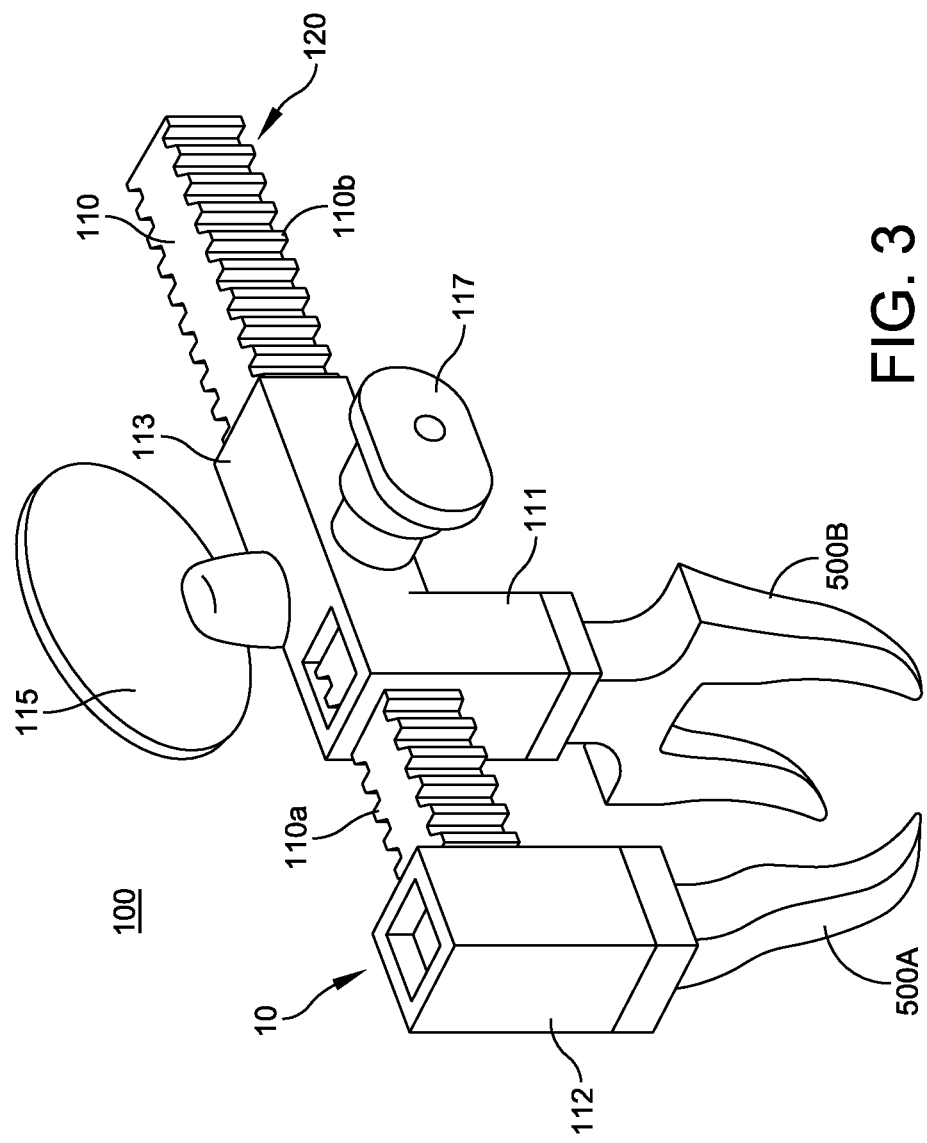
FIG. 3 is an illustration of and embodiment of the orthopedic device of FIG. 1 with 3-point bending yoke attachments.

An example of the orthopedic device 100 with 3-point bending yoke attachments 500A and 500B attached to the first and second arm members 111, 112 is shown in FIG. 3. Such 3-point bending yoke attachments can be used to accomplish radial distraction of a bone segment.

As shown in FIG. 2A, the outer ends of the first and second arm members 111, 112 are configured to receive attachments. As shown in FIG. 5C, the biaxial hinge block 130 is hingeably connected to an arm extension piece 111a, 112a which is configured to removably attach to the first and second arm members 111, 112. The specific structures that will enable such attachment between the first and second arm members and the arm extension pieces can be one of a variety of structures that are well known or obvious to one of ordinary skill in the art and need not be described in detail here.

Figure 4B:
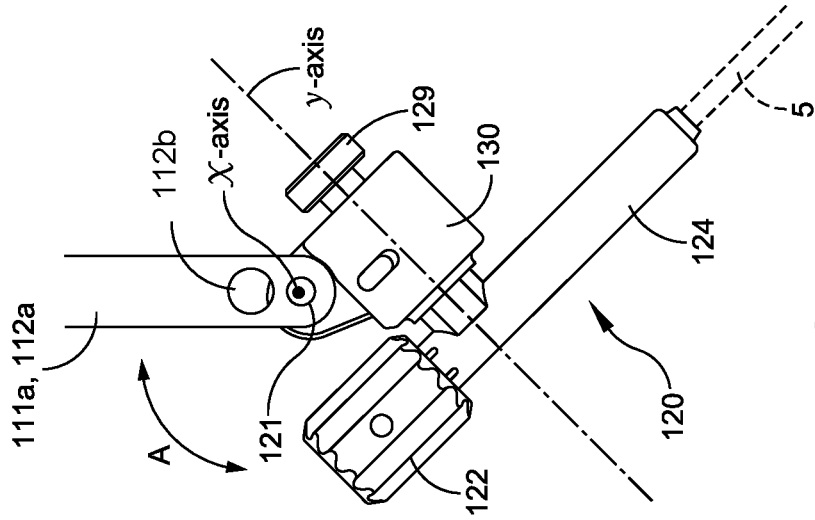
FIG. 4B is an illustration of the biaxially swiveling locking sleeve swiveled about the x-axis.
Figure 4A:
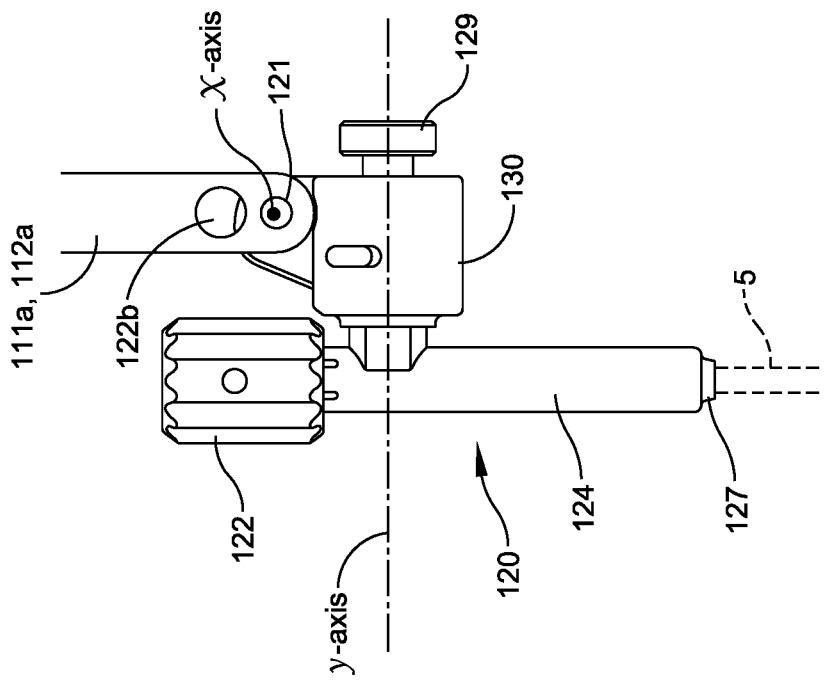
FIG. 4A is an illustration of a biaxially swiveling locking sleeve attachment in its straight position viewed along its x-axis.
Figure 5B:
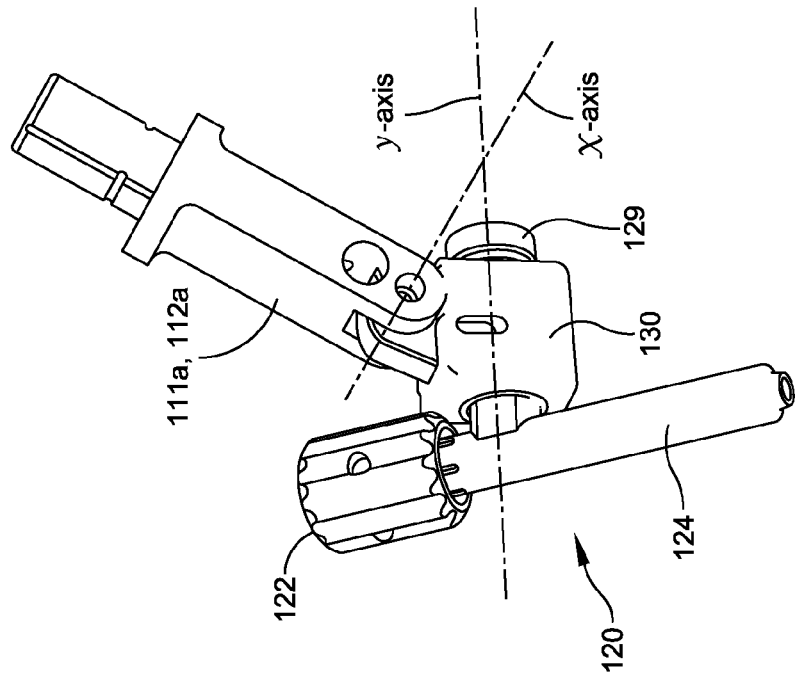
FIG. 5B is an illustration of the biaxially swiveling locking sleeve swiveled about the x-axis and the y-axis.
Figure 5A:
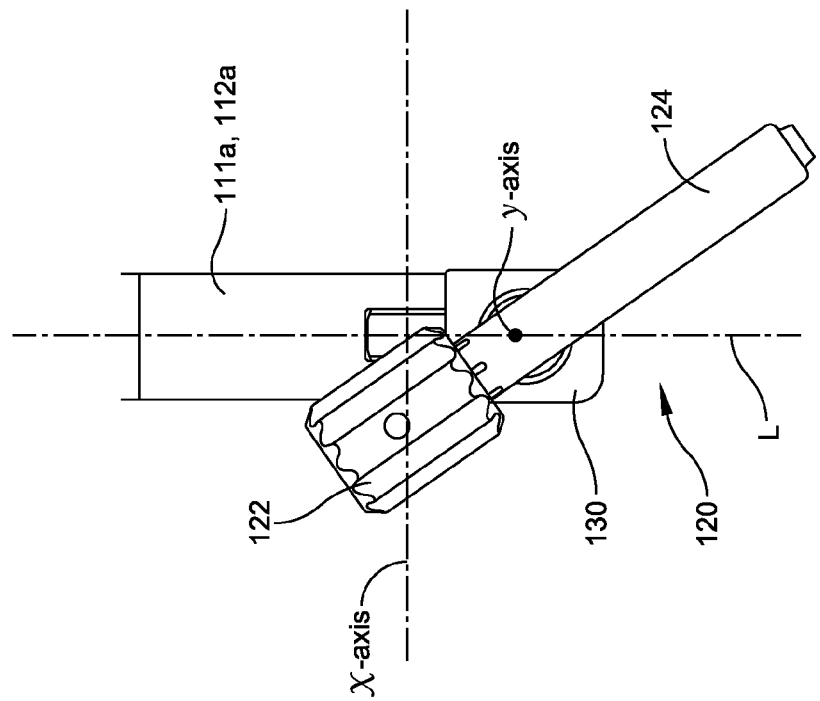
FIG. 5A is an illustration of the biaxially swiveling locking sleeve swiveled about its y-axis.

Referring to FIGS. 4A and 4B, the biaxial hinge block 130 includes a first hinge joint that swivels about a first swivel axis, x-axis. The first hinge joint allows the locking sleeve 120 to swivel about the x-axis in a first direction which is represented by the arrow A in FIG. 4B. The first hinge joint can include a swivel pin 121 forming the x-axis and connecting the biaxial hinge block 130 to the arm extension piece 111a, 112a. The biaxial hinge block 130 also includes a second hinge joint that swivels about a second swivel axis, y-axis, that is orthogonal to the first swivel axis. Thus, the biaxial hinge block 130 allows the locking sleeve 120 to swivel in two directions about the two orthogonally oriented swivel axes. FIG. 5A shows the locking sleeve 120 swiveled about the second swivel axis, y-axis, so that the locking sleeve 120 is tilted away from the longitudinal axis L of the arm extension pieces 111a, 112a. FIG. 5B shows an orthogonal projection view of the locking sleeve 120 swiveled about both swivel axes of the biaxial hinge block 130.

In the illustrated example, the first hinge joint is formed by a swivel pin 121 that is aligned with the x-axis and connects the biaxial hinge block 130 to the arm extension pieces 111a, 112a. The first swivel axis, x-axis, is oriented parallel to the elongated body 110 of the orthopedic device.

According to an aspect of the present disclosure, the first hinge joint can be configured and adapted to be normally locked at a desired swivel angle and prevented from swiveling about the first swivel axis, x-axis, by a spring-loaded locking pin 112b. When the spring-loaded locking pin 112b is pressed, the first hinge joint is unlocked and free to swivel about the x-axis.

The second hinge joint of the biaxial hinge block 130 will be described in more detail using the additional FIGS. 6A through 11B. The second hinge joint is formed by a swiveling shaft 125, that is orthogonally extending from the elongated shaft of the locking sleeve 120 and received in the biaxial hinge block 130 along the second swivel axis, y-axis. The swiveling shaft 125 is movable within the biaxial hinge block 130 along the second swivel axis between two positions. A locked first position that keeps the locking sleeve 120 in a non-swiveling position preventing the locking sleeve 120 from swiveling about the second swivel axis, and an unlocked second position allowing the locking sleeve 120 to swivel about the second swivel axis.

FIGS. 6A-7B show the swiveling shaft 125 in its unlocked second position within the biaxial hinge block 130, wherein the locking sleeve attachment 120 can swivel about the y-axis. FIG. 6A is an illustration of the locking sleeve attachment 120 connected to the biaxial hinge block 130 viewed along the y-axis showing the plane K-K extending through the center of the locking sleeve attachment 120 along which the cross-sectional view of FIG. 6B is taken. FIG. 6B is the cross-sectional view taken along K-K. FIG. 7A is the illustration of FIG. 6A showing the plane L-L extending off-center through the locking sleeve attachment 120 along which the cross-sectional view of FIG. 7B is taken. FIG. 7B is a cross-sectional view along L-L. The biaxial hinge block 130 is provided with a through-hole 131 for receiving the swiveling shaft 125 therethrough. The swiveling shaft 125 has an annular groove 126 and the biaxial hinge block 130 is provided with a locking key 140 that engages the annular groove 126 and keeps the locking sleeve 120 in the unlocked second position. The engaging relationship between the locking key 140 and the swiveling shaft 125 can be better seen in FIG. 10B in which only the locking sleeve's swiveling shaft 125 and the locking key 140 are shown without the biaxial hinge block 130. The locking key 140 sits within the annular groove 126 and prevents the swiveling shaft 125 from moving along the y-axis while allowing the swiveling shaft 125 and, thus, the locking sleeve 120 to swivel about the y-axis.

Figure 9B:
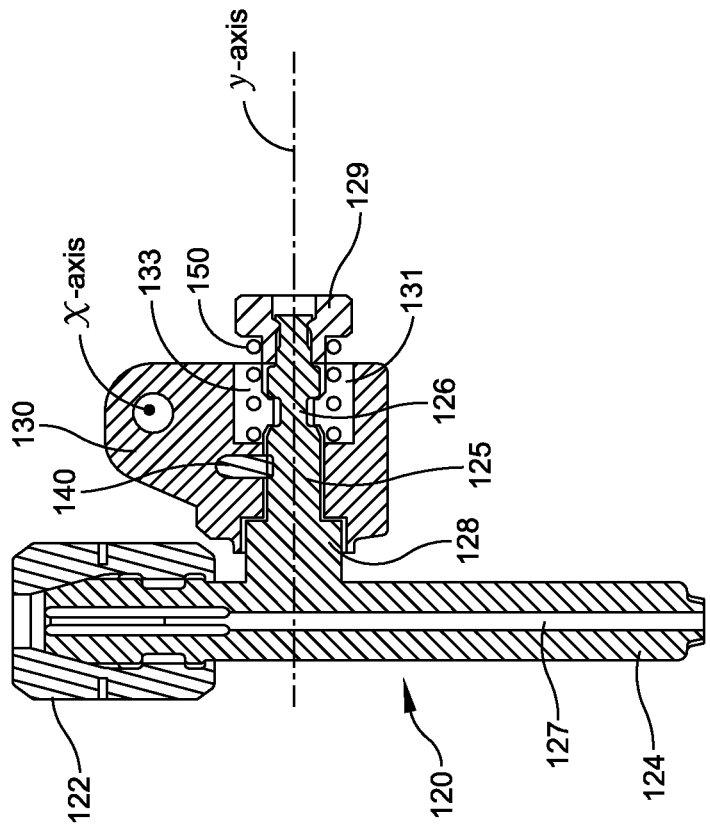
FIG. 9B is a cross-sectional view along N-N taken through the biaxially swiveling locking sleeve attachment in its swiveling position.
Figure 9A:
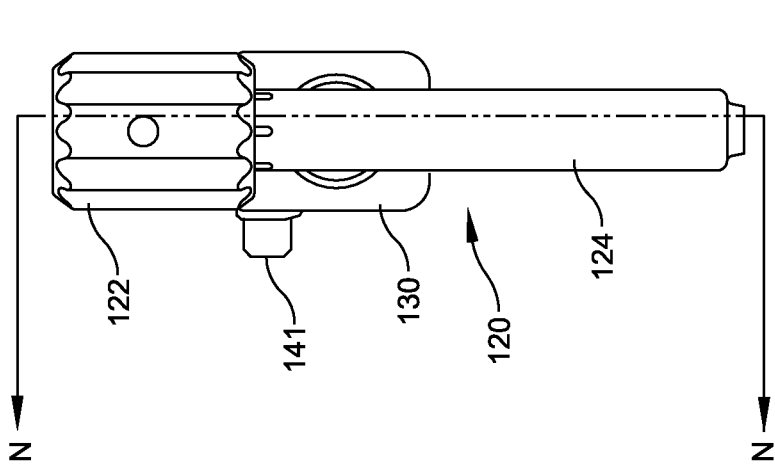
FIG. 9A is the illustration of FIG. 6A showing the plane N-N extending off-center through the locking sleeve along which the cross-sectional view of FIG. 9B is taken.

FIGS. 8A-9B show the swiveling shaft 125 in its locked first position, the non-swiveling position, within the biaxial hinge block 130. The locking sleeve attachment 120 is in a fixed orientation and cannot swivel about the y-axis. FIG. 8A is the same view as FIG. 6A but showing the plane M-M extending through the center of the locking sleeve along which the cross-sectional view of FIG. 8B is taken. FIG. 8B is a cross-sectional view taken along M-M. FIG. 9A is the same view as FIG. 6A but showing the plane N-N extending off-center through the locking sleeve along which the cross-sectional view of FIG. 9B is taken. FIG. 9B is a cross-sectional view taken along N-N. In the locked first position, the swiveling shaft 125 is pushed further into the through-hole 131 of the biaxial hinge block 130 so that the locking key 140 is no longer sitting within the annular groove 126. Referring to FIGS. 10A-11B, the swiveling shaft 125 is provided with one or more alignment tabs 128 near the base portion (the part of the elongated shaft 124 connected to the elongated shaft 124) of the swiveling shaft 125 and the through-hole 131 of the biaxial hinge block 130 has an alignment-tab-receiving end 132 (see FIG. 7B) that is configured and adapted to receive the alignment tabs 128. Preferably, the alignment tabs 128 are two tabs oppositely located on the base portion of the swiveling shaft but other non-symmetrically positioned arrangements are also contemplated.

The alignment-tab-receiving end 132 of the through-hole 131 has an opening outline that matches the transverse cross-sectional outline of the alignment tabs 128 so that in the locked first position, where the swiveling shaft 125 is pushed further into the through-hole 131, the alignment tabs 128 engage or mate with the alignment-tab-receiving end 132 and prevent the locking sleeve from swiveling about the y-axis.

In one embodiment, the locked first position holds the locking sleeve 120 in an orientation that keeps the elongated shaft 124 of the locking sleeve 120 in a parallel orientation with the arm members 111, 112 of the orthopedic device. In another embodiment, the alignment tabs 128 and the alignment-tab-receiving end 132 can be configured to hold the locking sleeve 120 in any desired angular orientation about the y-axis.

Referring to FIGS. 6A-9B, the swiveling shaft 125 is provided with an end cap 129 that captures a coil spring 150 inside an end-cap-receiving portion 133 of the through-hole 131. The coil spring is in a normally compressed state inside the end-cap-receiving portion 133 so that the coil spring is always urging against the end cap 129 pulling the swiveling shaft 125 further into the through-hole 131 and toward the locked first position shown in FIGS. 8A-9B.

Figure 11B:
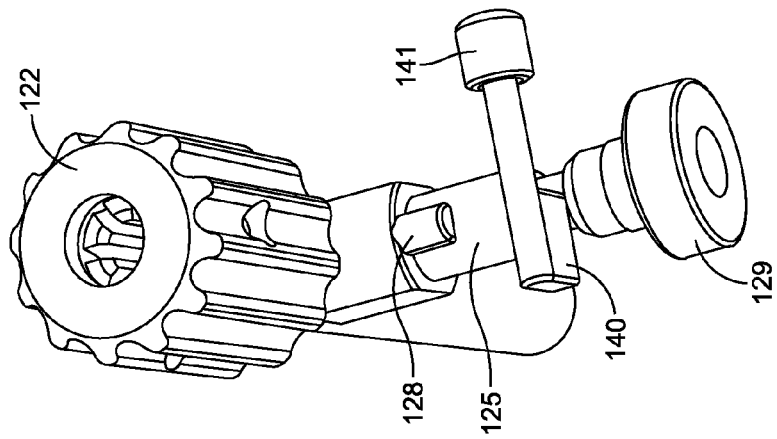
FIG. 11B is an illustration of the biaxially swiveling locking sleeve in the same configuration as in FIG. 10B viewed from a different angle.
Figure 11A:
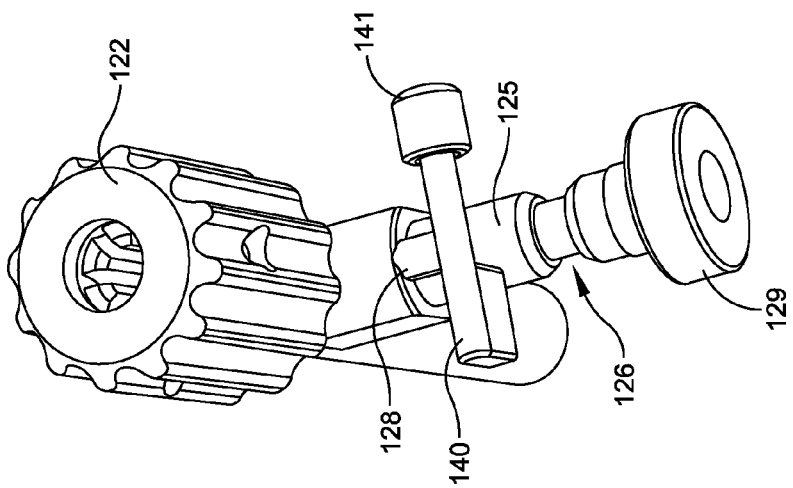
FIG. 11A is an illustration of the biaxially swiveling locking sleeve in the same configuration as in FIG. 10A viewed from a different angle.

FIGS. 10A and 11A show the positional relationship of the locking key 140 and the swiveling shaft 125 when the swiveling shaft 125 is in the locked first position. In the locked first position, the locking key 140 is not sitting in the annular groove 126.

According to an embodiment, the locking key 140 is spring-loaded within the biaxial hinge block 130 to be urged in the direction C shown in FIGS. 10A and 10B, which is transverse to the y-axis, the second swivel axis. To unlock the swiveling shaft 125 from the locked first position shown in FIGS. 9B and 10A, the end cap 129 of the swiveling shaft is pushed in the direction B shown in FIG. 10A. This moves the swiveling shaft 125 along the y-axis into its unlocked second position and the annular groove 126 comes in alignment with the locking key 140. Because the locking key 140 is spring-loaded and being urged in the direction C, the locking key 140 will slide into the annular groove 126 and prevents the swiveling shaft 125 from backing out and keeps the swiveling shaft 125 in its unlocked second position. To move the swiveling shaft 125 back to its non-swiveling first position, the end cap 141 of the locking key 140 is pushed in the direction opposite C, thus sliding the locking key 140 out of the annular groove 126. With the locking key 140 out of the annular groove 126, the spring-loaded swiveling shaft 125 will slide along the y-axis in direct opposite B and return to its first position if he alignment tabs 128 are aligned with the mating outline of the alignment-tab-receiving end 132 of the through-hole 131.

As described, the orthopedic device 100 of the present disclosure is a universal device that can be used for compression or distraction of bone parts that are secured to the first and second arm members 112, 111 by elongated pins, such as K-wires, locked into the elongated pin receiving bores 127 of the locking sleeves 120. Referring to FIG. 1, after the bone parts are secured, the movable second arm member 111 can be moved in compression direction 201 or distraction direction 202 by turning the turning key handle 115.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention. The scope of the invention disclosed herein is to be limited only by the following claims.

What is claimed is:

1. An orthopedic device comprising:
an elongated body having first and second ends;
a first arm member attached to and extending away from said first end and terminating at an outer end;
a second arm member extending from said elongated body and having a base portion and an outer end, wherein the base portion is configured and adapted to engage the elongated body and allow the second arm member to be longitudinally movable along said elongated body, said second arm member extending from the elongated body in a same direction as the first arm member; and
a locking sleeve hingeably connected to the outer end of each of the first and second arm members by a biaxial hinge block, wherein the locking sleeve is configured for receiving and locking on to an elongated pin and said biaxial hinge block is configured to allow each of the locking sleeve to swivel in two different directions with respect to its corresponding arm member about two orthogonally oriented swivel axes;
wherein said locking sleeve is provided with a swiveling shaft orthogonally extending from an elongated shaft, said locking sleeve being connected to the biaxial hinge block by the swiveling shaft and received in the biaxial hinge block along one of the two orthogonally oriented swivel axes such that a first of the two orthogonally oriented swivel axes is oriented parallel to the elongated body of the orthopedic device and the swiveling shaft of the locking sleeve is received in the biaxial hinge block along a second of the two orthogonally oriented swivel axis, and the swiveling shaft is movable within the biaxial hinge block along the second swivel axis between two positions, a first position that prevents the locking sleeve from swiveling about the second swivel axis and a second position allowing the locking sleeve to swivel about a second of the two orthogonally oriented swivel axis.

2. The orthopedic device of claim 1, wherein said locking sleeve comprises an elongated pin receiving bore extending therethrough and a collet provided at one end of the elongated shaft, said collet comprising a plurality of collet arms provided with screw threads integrally formed on their exterior surfaces, and a collet nut that is threadably engaged to the collet for locking the elongated pin that is received in the elongated pin receiving bore.

3. The orthopedic device of claim 1, wherein the biaxial hinge block provided with a through-hole for receiving the swiveling shaft therethrough, the through-hole having an end-cap-receiving portion, wherein the swiveling shaft is provided with an end cap that captures a coil spring inside the end-cap-receiving portion of the through-hole, wherein the coil spring is in a normally compressed state inside the end-cap-receiving portion urging against the end cap and pulling the swiveling shaft further into the through-hole toward the first position.

4. The orthopedic device of claim 1, wherein the swiveling shaft is provided with one or more alignment tabs near its base portion and a through-hole has an alignment-tab-receiving end that is configured and adapted to receive the one or more alignment tabs, wherein the alignment-tab-receiving end of the through-hole has an opening outline that matches transverse cross-sectional outline of the one or more alignment tabs thereby when in the first position, the one or more alignment tabs engage with the alignment-tabreceiving end and prevent the locking sleeve from swiveling about the second of the two orthogonally oriented swivel axis.

5. The orthopedic device of claim 1, wherein the first position holds the locking sleeve in an orientation that keeps the elongated shaft of the locking sleeve in a parallel orientation with the arm members of the orthopedic device.

6. The orthopedic device of claim 1, further comprising a locking key provided in the biaxial hinge block that engages the swiveling shaft to lock the swiveling shaft in the second position.

7. The orthopedic device of claim 1, wherein a locking key is spring-loaded within the biaxial hinge block to be urged in the direction transverse to the second of the two orthogonally oriented swivel axis.

8. The orthopedic device of claim 6, wherein the swiveling shaft is configured with an annular groove that engages the locking key when the swiveling shaft is in the second position.

9. The orthopedic device of claim 8, wherein when the swiveling shaft is in the first position, the locking key and the annular groove are not engaged while alignment tabs provided on the swiveling shaft and an alignment-tab-receiving end are engaged and thus preventing the swiveling shaft from swiveling in the second of the two orthogonally oriented swivel axis.

10. An assembly comprising:
a biaxial hinge block; and
a locking sleeve, wherein the biaxial hinge block and the locking sleeve are configured to hingeably connect the locking sleeve to an arm member of an orthopedic device, said biaxial hinge block being configured to allow the locking sleeve to swivel in two different directions with respect to the arm member about two orthogonally oriented swivel axes;
wherein said locking sleeve is provided with a swiveling shaft orthogonally extending from an elongated shaft, said locking sleeve being connected to the biaxial hinge block by the swiveling shaft and received in the biaxial hinge block along one of the two orthogonally oriented swivel axes such that a first of the two orthogonally oriented swivel axes is oriented parallel to an elongated body of the orthopedic device and the swiveling shaft of the locking sleeve is received in the biaxial hinge block along a second of the two orthogonally oriented swivel axis; and the swiveling shaft is movable within the biaxial hinge block along the second swivel axis between two positions, a first position that prevents the locking sleeve from swiveling about the second swivel axis and a second position allowing the locking sleeve to swivel about a second of the two orthogonally oriented swivel axis.

11. The assembly of claim 10 wherein said locking sleeve comprises an elongated pin receiving bore extending therethrough and a collet provided at one end of the elongated shaft, said collet comprising a plurality of collet arms provided with screw threads integrally formed on their exterior surfaces, and a collet nut that is threadably engaged to the collet for locking an elongated pin that is received in the elongated pin receiving bore.

12. The assembly of claim 10, wherein the biaxial hinge block provided with a through-hole for receiving the swiveling shaft therethrough, the through-hole having an end-cap-receiving portion, wherein the swiveling shaft is provided with an end cap that captures a coil spring inside the end-cap-receiving portion of the through-hole, wherein the coil spring is in a normally compressed state inside the end-cap-receiving portion urging against the end cap and pulling the swiveling shaft further into the through-hole toward the first position.

13. The assembly of claim 10, wherein the swiveling shaft is provided with one or more alignment tabs near its base portion and a through-hole has an alignment-tab-receiving end that is configured and adapted to receive the one or more alignment tabs, wherein the alignment-tab-receiving end of the through-hole has an opening outline that matches transverse cross-sectional outline of the one or more alignment tabs thereby when in the first position, the one or more alignment tabs engage with the alignment-tab-receiving end and prevent the locking sleeve from swiveling about the second of the two orthogonally oriented swivel axis.

14. The assembly of claim 10, wherein the first position holds the locking sleeve in an orientation that keeps the elongated shaft of the locking sleeve in a parallel orientation with an arm member of the orthopedic device.

15. The assembly of claim 10, further comprising a locking key provided in the biaxial hinge block that engages the swiveling shaft to lock the swiveling shaft in the second position.

16. The assembly of claim 10, wherein a locking key is spring-loaded within the biaxial hinge block to be urged in the direction transverse to the second of the two orthogonally oriented swivel axis.

17. The assembly of claim 15, wherein the swiveling shaft is configured with an annular groove that engages the locking key when the swiveling shaft is in the second position.

18. The assembly of claim 17, wherein when the swiveling shaft is in the first position, the locking key and the annular groove are not engaged while alignment tabs provided on the swiveling shaft and an alignment-tab-receiving end are engaged and thus preventing the swiveling shaft from swiveling in the second of the two orthogonally oriented swivel axis.

* * * * *